US011231418B2

(12) United States Patent
Renaudineau et al.

(10) Patent No.: US 11,231,418 B2
(45) Date of Patent: Jan. 25, 2022

(54) PROCESSES FOR THE DIAGNOSIS, PROGNOSIS AND MONITORING OF THE PROGRESSION OF CHRONIC LYMPHOID LEUKAEMIA (CLL) AND/OR OF SYSTEMIC LUPUS ERYTHEMATOSUS (SLE) USING MEMBRANE STIM 1

(71) Applicants: UNIVERSITÉ DE BRETAGNE OCCIDENTALE—UBO, Brest (FR); INSERM, Paris (FR); CENTRE HOSPITALIER RÉGIONAL ET UNIVERSITAIRE DE BREST, Brest (FR)

(72) Inventors: Yves Renaudineau, Brest (FR); Olivier Mignen, Logonna Daoulas (FR); Marjolaine Debant, Brest (FR); Christelle Le Dantec, Plougasnou (FR); Jacques Olivier Pers, Brest (FR)

(73) Assignees: UNIVERSITÉ DE BRETAGNE OCCIDENTALE—UBO, Brest (FR); INSERM, Paris (FR); CENTRE HOSPITALIER RÉGIONAL ET UNIVERSITAIRE DE BREST, Brest (FR)

( * ) Notice: Subject to any disclaimer, the term of this patent is extended or adjusted under 35 U.S.C. 154(b) by 270 days.

(21) Appl. No.: 15/554,166

(22) PCT Filed: Feb. 26, 2016

(86) PCT No.: PCT/EP2016/054039
§ 371 (c)(1),
(2) Date: Aug. 28, 2017

(87) PCT Pub. No.: WO2016/135273
PCT Pub. Date: Sep. 1, 2016

(65) Prior Publication Data
US 2018/0267035 A1 Sep. 20, 2018

(30) Foreign Application Priority Data
Feb. 26, 2015 (EP) .................................... 15156694

(51) Int. Cl.
| A61K 33/00 | (2006.01) |
| G01N 33/564 | (2006.01) |
| G01N 33/574 | (2006.01) |
| G01N 33/68 | (2006.01) |

(52) U.S. Cl.
CPC ..... *G01N 33/564* (2013.01); *G01N 33/57426* (2013.01); *G01N 33/6893* (2013.01); *G01N 33/574* (2013.01); *G01N 2800/104* (2013.01); *G01N 2800/52* (2013.01); *G01N 2800/7028* (2013.01)

(58) Field of Classification Search
CPC .................................................. G01N 33/574
See application file for complete search history.

(56) References Cited

U.S. PATENT DOCUMENTS

| 2008/0081339 A1* | 4/2008 | Liu .................. G01N 33/57434 435/6.14 |
| 2008/0293092 A1 | 11/2008 | Stauderman et al. |
| 2011/0190157 A1* | 8/2011 | Kipps .................. C12Q 1/6886 506/9 |
| 2012/0128586 A1 | 5/2012 | Calissano et al. |
| 2018/0201901 A1* | 7/2018 | Duchateau ............. A61K 35/17 |

FOREIGN PATENT DOCUMENTS

| CA | 2547901 A1 | 12/2007 |
| EP | 1905841 A1 | 4/2008 |
| JP | 2011523455 A | 8/2011 |
| WO | WO2009132058 A2 | 10/2009 |

OTHER PUBLICATIONS

Spassova et al. (Proc. Natl. Acad. Sci. USA. Mar. 14, 2006; 103 (11): 4040-5).*
Horinouchi et al. (Biochem. Biophys. Res. Commun. Nov. 16, 2012; 428 (2): 252-8).*
Manji et al. (Biochim. Biophys. Acta. Aug. 31, 2000; 1481 (1): 147-55).*
Mignen et al. (J. Physiol. Mar. 15, 2007; 579 (Pt. 3): 703-15).*
Zhang et al. (Nature. Oct. 6, 2005; 437 (7060): 902-5).*
Wang et al. (Cell Physiol. Biochem. 2018; 48 (6): 2273-2285).*
Debant et al. (J. Immunother Cancer. Apr. 23, 2019; 7 (1): 111; pp. 1-13).*
Renaudineau et al. (Annals of the Rheumatic Diseases. 2013; 72: A30; pp. 1).*
Várnai et al. (J. Biol. Chem. Oct. 5, 2007; 282 (40): 29678-90).*
Muik et al. (J. Biol. Chem. Mar. 27, 2009; 284 (13): 8421-6).*
Shuttleworth et al. (Cell Calcium. Aug. 2007; 42 (2):183-91).*
Renaudineau et al. (Ann. Rheum. Dis. 2013; 72 (Suppl. 1): A5.1; p. A30).*
Liou et al. (Proc. Natl. Acad. Sci. USA. May 29, 2007; 104 (22): 9301-6).*
Mukherjee et al. (Biochim. Biophys. Acta. Oct. 2014; 1843 (10): 2307-14).*
Petri M; Orbai AM; Alarcón GS; Gordon C; Merrill JT; Fortin PR et al., "Derivation and validation of the Systemic Lupus International Collaborating Clinics classification criteria for systemic lupus erythematosus", Arthritis Rheum., (2012), vol. 64, doi:doi:10.1002/art.34473, pp. 2677-2686.

(Continued)

*Primary Examiner* — Stephen L Rawlings
(74) *Attorney, Agent, or Firm* — Kenealy Vaidya LLP

(57) ABSTRACT

Some embodiments are directed to a process for the diagnosis of systemic lupus erythematosus (SLE) and/or of chronic lymphoid leukaemia (CLL) of a subject who may be suffering therefrom, comprising the in vitro detection of the expression of the fraction of the STIM1 protein located at the cell plasma membrane in a biological sample from human and mice. Some other embodiments are directed to a process for predicting the progression and/or monitoring the progression of CLL and/or of SLE, comprising the in vitro detection of the expression of the fraction of the STIM1 protein located at the cell plasma membrane.

17 Claims, 5 Drawing Sheets

Specification includes a Sequence Listing.

(56) References Cited

OTHER PUBLICATIONS

Binet JL; Leporier M; Dighiero G; Charron D; D'Athis P; Vaugier G; Beral HM; Natali JC; Raphael M; Nizet B, "A clinical staging system for chronic lymphocytic leukaemia: prognostic significance", Cancer, (1977), vol. 40, pp. 855-864.

Pflug N; Bahlo J; Shanafelt TD; Eichhorst BF; Bergmann MA; Elter T et al., "Development of a comprehensive prognostic index for patients with chronic lymphocytic leukaemia", Blood, (2014), vol. 124, pp. 49-62.

Novak U; Oppliger Leibundgut E; Hager J; Muhiematter D; Jotterand M; Besse C; Leupin N; Ratschiller D; Papp J; Kearsey G, "A high-resolution allelotype of B-cell chronic lymphocytic leukaemia (B-CLL", Blood, (2002), vol. 100, pp. 1787-1794.

Liossis SN; Kovacs B; Dennis G; Kammer GM; Tsokos GC, "B cells from patients with systemic lupus erythematosus display abnormal antigen receptor-mediated early signal transduction events", J Clin Invest., (1996), vol. 98, pp. 2549-2557.

Duhren-Von Minden M; Obelhart R; Schneider D; Wossning T; Bach MP; Buchner M et al., "Chronic lymphocytic leukaemia is driven by antigen-independent cell-autonomous signalling", Nature, (2012), vol. 489, doi:doi:10.1038/nature11309, pp. 309-313.

Shlomchik, M. J.; Madio, M. P.; Ni, D.; Trounstine, M.; Huszar, D., "The role of B cells in IprIpr-induced autoimmunity", J. Exp. Med., (1994), vol. 180, pp. 1295-1306.

Mignen O; Thompson JL; Shuttleworth TJ, "STIM1 regulates Ca2+ entry via arachidonate-regulated Ca2+—selective (ARC) channels without store depletion or translocation to the plasma membrane", J Physiol., (2007), vol. 579, doi:doi:10.1113/jphysiol.2006.122432, pp. 703-715.

Fali, T., "A3.20 The calcium sensor stromal interaction molecule 1 (STIM1) controls regulatory B cell functions and its activity is impaired in Systemic Lupus Erythematosus patents," Ann. Rheum. Dis. 2014, 73 Suppl. 1, pp. A49-A50, XP055201603.

Renaudineau, Y., "Abnormal calcium influx in T and B lymphocytes from systemic lupus erythematosus patients is related to STIM-1 over-expression," Ann. Rheum. Dis. 2013, 72 Suppl. 1, pp. A30-A30, XP055201611.

Chen, N., et al., "Role of high expression of IL-9 in prognosis of CLL," Int. J. Clin. Exp. Pathol. 2014;7(2):716-721, XP055201650.

Bombardier, C., et al., "Derivation of the Sledai A Disease Activity Index for Lupus Patients," Arthritis & Rheumatism 1992;35(6):630-640.

International Search Report for PCT/EP2016/054039 (dated Apr. 28, 2016).

Written Opinion for PCT/EP2016/054039 (dated Apr. 28, 2016).

\* cited by examiner

SEQUENCE LISTING

<160> NUMBER OF SEQ ID NOS: 7

<210> SEQ ID NO 1
<211> LENGTH: 685
<212> TYPE: PRT
<213> ORGANISM: Homo sapiens

<400> SEQUENCE: 1

Met Asp Val Cys Val Arg Leu Ala Leu Trp Leu Leu Trp Gly Leu Leu
1               5                   10                  15

Leu His Gln Gly Gln Ser Leu Ser His Ser His Ser Glu Lys Ala Thr
            20                  25                  30

Gly Thr Ser Ser Gly Ala Asn Ser Glu Glu Ser Thr Ala Ala Glu Phe
        35                  40                  45

Cys Arg Ile Asp Lys Pro Leu Cys His Ser Glu Asp Glu Lys Leu Ser
    50                  55                  60

```
Phe Glu Ala Val Arg Asn Ile His Lys Leu Met Asp Asp Ala Asn
 65                  70                  75                  80

Gly Asp Val Asp Val Glu Glu Ser Asp Glu Phe Leu Arg Glu Asp Leu
                 85                  90                  95

Asn Tyr His Asp Pro Thr Val Lys His Ser Thr Phe His Gly Glu Asp
                100                 105                 110

Lys Leu Ile Ser Val Glu Asp Leu Trp Lys Ala Trp Lys Ser Ser Glu
            115                 120                 125

Val Tyr Asn Trp Thr Val Asp Glu Val Val Gln Trp Leu Ile Thr Tyr
        130                 135                 140

Val Glu Leu Pro Gln Tyr Glu Glu Thr Phe Arg Lys Leu Gln Leu Ser
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His
        195                 200                 205

Asn His Leu Lys Asp Phe Met Leu Val Val Ser Ile Val Ile Gly Val
210                 215                 220

Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
                245                 250                 255

Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
        275                 280                 285

Glu Ile Asn Leu Ala Lys Gln Glu Ala Gln Arg Leu Lys Glu Leu Arg
        290                 295                 300

Glu Gly Thr Glu Asn Glu Arg Ser Arg Gln Lys Tyr Ala Glu Glu Glu
305                 310                 315                 320

Leu Glu Gln Val Arg Glu Ala Leu Arg Lys Ala Glu Lys Glu Leu Glu
                325                 330                 335

Ser His Ser Ser Trp Tyr Ala Pro Glu Ala Leu Gln Lys Trp Leu Gln
            340                 345                 350

Leu Thr His Glu Val Glu Val Gln Tyr Tyr Asn Ile Lys Lys Gln Asn
        355                 360                 365

Ala Glu Lys Gln Leu Leu Val Ala Lys Glu Gly Ala Glu Lys Ile Lys
        370                 375                 380

Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
                405                 410                 415

Ser Glu Val Thr Ala Ala Leu Arg Glu Arg Leu His Arg Trp Gln Gln
            420                 425                 430

Ile Glu Ile Leu Cys Gly Phe Gln Ile Val Asn Asn Pro Gly Ile His
        435                 440                 445

Ser Leu Val Ala Ala Leu Asn Ile Asp Pro Ser Trp Met Gly Ser Thr
        450                 455                 460

Arg Pro Asn Pro Ala His Phe Ile Met Thr Asp Asp Val Asp Met
465                 470                 475                 480

Asp Glu Glu Ile Val Ser Pro Leu Ser Met Gln Ser Pro Ser Leu Gln
```

```
                485                 490                 495
Ser Ser Val Arg Gln Arg Leu Thr Glu Pro Gln His Gly Leu Gly Ser
            500                 505                 510

Gln Arg Asp Leu Thr His Ser Asp Ser Glu Ser Ser Leu His Met Ser
            515                 520                 525

Asp Arg Gln Arg Val Ala Pro Lys Pro Pro Gln Met Ser Arg Ala Ala
            530                 535                 540

Asp Glu Ala Leu Asn Ala Met Thr Ser Asn Gly Ser His Arg Leu Ile
545                 550                 555                 560

Glu Gly Val His Pro Gly Ser Leu Val Glu Lys Leu Pro Asp Ser Pro
                565                 570                 575

Ala Leu Ala Lys Lys Ala Leu Leu Ala Leu Asn His Gly Leu Asp Lys
            580                 585                 590

Ala His Ser Leu Met Glu Leu Ser Pro Ser Ala Pro Pro Gly Gly Ser
            595                 600                 605

Pro His Leu Asp Ser Ser Arg Ser His Ser Pro Ser Ser Pro Asp Pro
        610                 615                 620

Asp Thr Pro Ser Pro Val Gly Asp Ser Arg Ala Leu Gln Ala Ser Arg
625                 630                 635                 640

Asn Thr Arg Ile Pro His Leu Ala Gly Lys Lys Ala Val Ala Glu Glu
                645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Lys Pro Leu Lys Lys
            675                 680                 685

<210> SEQ ID NO 2
<211> LENGTH: 4062
<212> TYPE: DNA
<213> ORGANISM: Homo sapiens

<400> SEQUENCE: 2
ctggacctgg gcaccgccag ccgcctgggc acgggactgg gcggggcgc tgacctcggc      60 ctaggaggcc caggatcccg gagacgcccg cgccctcagg accctgcggg tcgcacgccc    120
tccccagctt ctgctgctcg ccgctcttcg gcagggcgag gtcaggtgcc cccttctcgc    180
ctctcttctc ttctcttctc ttcctcctcc acttctgtgc ccgcgcgagac tccgccgcc    240 cccttccgca ggggtgtagt aatctgcgga gctgacagca gccccgcagc caccctgccc    300
gaagtctccg gaagcggcac gagctcaggc cgccgcagcc ccgcggacc cactgttgga    360 cctgaggagc cagccctcct cccgcaccca aacttggagc acttgacctt tggctgttgg    420 aggggggcagg ctcgcgggtg gctggacagc tgccgagccg cgagggcatc ttgcctggag    480
accgtcggct gcactccggg gctcctggct ttgcctctgg gatcccgagg tgtccacatc    540
agacgcatgt tgactgagac ctagagtcat ggatgtatgc gtccgtcttg ccctgtggct    600
cctctgggga ctcctcctgc accagggcca gagcctcagc catagtcaca gtgagaaggc    660
gacaggaacc agctcggggg ccaactctga ggagtccact gcagcagagt tttgccgaat    720
tgacaagccc ctgtgtcaca gtgaggatga gaaactcagc ttcgaggcag tccgtaacat    780
ccacaaactg atggacgatg atgccaatgg tgatgtggat gtggaagaaa gtgatgagtt    840
cctgagggaa gacctcaatt accatgaccc aacagtgaaa cacagcacct tccatggtga    900
ggataagctc atcagcgtgg aggacctgtg aaggcatgg aagtcatcag aagtatacaa    960
ttggaccgtg gatgaggtgg tacagtggct gatcacatat gtggagctgc ctcagtatga   1020
```

```
ggagaccttc cggaagctgc agctcagtgg ccatgccatg ccaaggctgg ctgtcaccaa    1080
caccaccatg acagggactg tgctgaagat gacagaccgg agtcatcggc agaagctgca    1140
gctgaaggct ctggatacag tgctctttgg gcctcctctc ttgactcgcc ataatcacct    1200
caaggacttc atgctggtgg tgtctatcgt tattggtgtg ggcggctgct ggtttgccta    1260
tatccagaac cgttactcca aggagcacat gaagaagatg atgaaggact ggaggggtt    1320 acaccgagct gagcagagtc tgcatgacct tcaggaaagg ctgcacaagg cccaggagga    1380
gcaccgcaca gtggaggtgg agaaggtcca tctggaaaag aagctgcgcg atgagatcaa    1440
ccttgctaag caggaagccc agcggctgaa ggagctgcgg gagggtactg agaatgagcg    1500
gagccgccaa aaatatgctg aggaggagtt ggagcaggtt cgggaggcct tgaggaaagc    1560
agagaaggag ctagaatctc acagctcatg gtatgctcca gaggcccttc agaagtggct    1620
gcagctgaca catgaggtgg aggtgcaata ttacaacatc aagaagcaaa atgctgagaa    1680
gcagctgctg gtggccaagg aggggctga aagataaaa agaagagaa acacactctt    1740 tggcaccttc cacgtggccc acagctcttc cctggatgat gtagatcata aaattctaac    1800
agctaagcaa gcactgagcg aggtgacagc agcattgcgg gagcgcctgc accgctggca    1860
acagatcgag atcctctgtg gcttccagat tgtcaacaac cctggcatcc actcactggt    1920
ggctgccctc aacatagacc ccagctggat gggcagtaca cgcccaacc ctgctcactt    1980 catcatgact gacgacgtgg atgacatgga tgaggagatt gtgtctccct tgtccatgca    2040
gtcccctagc ctgcagagca gtgttcggca gcgcctgacg gagccacagc atggcctggg    2100
atctcagagg gatttgaccc cattccgatt cggagtcctcc ctccacatga gtgaccgcca    2160
gcgtgtggcc cccaaacctc ctcagatgag ccgtgctgca gacgaggctc tcaatgccat    2220
gacttccaat ggcagccacc ggctgatcga gggggtccac ccagggtctc tggtggagaa    2280
actgcctgac agccctgccc tggccaagaa ggcattactg cgcgctgaacc atgggctgga    2340 caaggcccac agcctgatgg agctgagccc ctcagcccca cctggtggct ctccacattt    2400
ggattcttcc cgttctcaca gccccagctc cccagaccca gacacaccat ctccagttgg    2460
ggacagccga gccctgcaag ccagccgaaa cacacgcatt ccccacctgg ctggcaagaa    2520
ggctgtggct gaggaggata atggctctat tggcgaggaa acagactcca gcccaggccg    2580
gaagaagttt cccctcaaaa tctttaagaa gcctcttaag aagtaggcag gatggggtgg    2640
cagtaaaggg acagcttgtc cttccctggg tgttctgtct ctccttccct cccttccttc    2700
aagataactg gccccaagag tggggcatgg gaagggctgg tccaggggtc tgggcactgt    2760
acatacctgc ccccctcatcc ttgggtcctt cattattatt tattaactga ccaccatggc    2820
ctgcctgccc tgcctccgtc caaccatgg gctgctgctg tcactccctc tccacttcag    2880
tgcatgtctt agttgctgtt ccctcagctc ccagctccac ctctggggtt cagcttctgt    2940
ctctgctgtc ccagttttga ggtttggttt cttgttgctg tctcttgctt tcgggctcct    3000
ccctcccacc actccccaac ttcccctagc agttgcaggg aagataggac gagtagcttc    3060
tgacatgtgt gcctcagatc tgttccaccc cactcacagt ggttctgttt gctccagact    3120
ggggctaggg cctaatcttt gaagtttgtt ctttggtatt gatgtgggtc agaaggagcc    3180
tcatcctaat ctcactcagg cctccaggga tccatggggg agtgaaacca attctcagag    3240
aacaacccac cagagacttt taaagagagg ccaggcttgg gaatgggttg ggagaggcat    3300
ctgttcattg gagcatgagt ggatgccaga actgtaggtt ataaggcagt cacttttct    3360
```

```
ctctactccc acccacacct gcctccctct taccctgct ccccacact gcaggaggat    3420
ttgtctctaa gaggtgctgc cccaaagctc cccaagcatc aatactccta gggctcagga    3480
caagtggctc ccctggccag gagagccaca gccatgatac agggtctta tggagccctg    3540
gagttgttgg gcaaggatgc tgtcattttt tgaaccaaaa gacaaacagg ttaaaaggaa    3600
aaaaagtaat ctgaatttcc caagtgccta cgctgcatat tccccttgtt agatccatt    3660
ttcatgttac tttgtagcct tggccagagg ctcaaaaagg acacaaccag tttgggaag    3720
gggtggctaa ggaagatggt ataggtgaag gcggctgtgt gaccactttc ccccacccctt   3780
cccaccctct agacaactct ctcccttacc tgtttttgct atggctgtaa aggtattttt    3840
cctctgcccc actccctgcc atacctttat cctgggatcc tattttgggc ctggggtggg   3900
tatacctggg gctggtctta ggagggtgct aggctgcaga ctgccttgta ctccctggac    3960
accctcaaat ggggttttct gtgttatttc ataaaattct ttgaagtcca ataaagcatg    4020
taggagattt taaccactaa aaaaaaaaaa aaaaaaaaa aa                        4062
```

<210> SEQ ID NO 3
<211> LENGTH: 191
<212> TYPE: PRT
<213> ORGANISM: Homo sapiens

<400> SEQUENCE: 3

```
Leu Ser His Ser His Ser Glu Lys Ala Thr Gly Thr Ser Ser Gly Ala
1               5                   10                  15

Asn Ser Glu Glu Ser Thr Ala Ala Glu Phe Cys Arg Ile Asp Lys Pro
            20                  25                  30

Leu Cys His Ser Glu Asp Glu Lys Leu Ser Phe Glu Ala Val Arg Asn
        35                  40                  45

Ile His Lys Leu Met Asp Asp Ala Asn Gly Asp Val Asp Val Glu
    50                  55                  60

Glu Ser Asp Glu Phe Leu Arg Glu Asp Leu Asn Tyr His Asp Pro Thr
65                  70                  75                  80

Val Lys His Ser Thr Phe His Gly Glu Asp Lys Leu Ile Ser Val Glu
                85                  90                  95

Asp Leu Trp Lys Ala Trp Lys Ser Ser Glu Val Tyr Asn Trp Thr Val
            100                 105                 110

Asp Glu Val Val Gln Trp Leu Ile Thr Tyr Val Glu Leu Pro Gln Tyr
        115                 120                 125

Glu Glu Thr Phe Arg Lys Leu Gln Leu Ser Gly His Ala Met Pro Arg
    130                 135                 140

Leu Ala Val Thr Asn Thr Thr Met Thr Gly Thr Val Leu Lys Met Thr
145                 150                 155                 160

Asp Arg Ser His Arg Gln Lys Leu Gln Leu Lys Ala Leu Asp Thr Val
                165                 170                 175

Leu Phe Gly Pro Pro Leu Leu Thr Arg His Asn His Leu Lys Asp
            180                 185                 190
```

<210> SEQ ID NO 4
<211> LENGTH: 21
<212> TYPE: DNA
<213> ORGANISM: Artificial Sequence
<220> FEATURE:
<223> OTHER INFORMATION: Forward primer

<400> SEQUENCE: 4
tctagaactg aggcgagtgg a                                              21

```
<210> SEQ ID NO 5
<211> LENGTH: 20
<212> TYPE: DNA
<213> ORGANISM: Artificial Sequence
<220> FEATURE:
<223> OTHER INFORMATION: Reverse primer

<400> SEQUENCE: 5
gcgctagtct ttgccaggat                                                    20

<210> SEQ ID NO 6
<211> LENGTH: 20
<212> TYPE: DNA
<213> ORGANISM: Artificial Sequence
<220> FEATURE:
<223> OTHER INFORMATION: Forward primer

<400> SEQUENCE: 6
agcacttgac ctttggctgt                                                    20

<210> SEQ ID NO 7
<211> LENGTH: 20
<212> TYPE: DNA
<213> ORGANISM: Artificial Sequence
<220> FEATURE:
<223> OTHER INFORMATION: Reverse primer

<400> SEQUENCE: 7
atttcaactt gcccacttcg                                                    20
```

PROCESSES FOR THE DIAGNOSIS, PROGNOSIS AND MONITORING OF THE PROGRESSION OF CHRONIC LYMPHOID LEUKAEMIA (CLL) AND/OR OF SYSTEMIC LUPUS ERYTHEMATOSUS (SLE) USING MEMBRANE STIM 1

CROSS REFERENCE TO RELATED APPLICATIONS

This application is a national phase filing under 35 C.F.R. § 371 of and claims priority to PCT Patent Application No. PCT/EP2016/054039, filed on Feb. 26, 2016, which claims the priority benefit under 35 U.S.C. § 119 of European Patent Application Nos 15156694.0, filed on Feb. 26, 2015, the contents of each of which are hereby incorporated in their entireties by reference.

BACKGROUND

Some embodiments relate to a process for the diagnosis of Systemic Lupus Erythematosus (SLE) and/or of Chronic Lymphoid Leukaemia (CLL), and also to a process for predicting the progression and/or monitoring the progression of CLL and/or of SLE.

Some embodiments have uses in the therapeutic field, in particular in the diagnostic field.

In the description below, the references between square brackets ([ ]) refer back to the list of references presented at the end of the text.

Systemic Lupus Erythematosus (SLE) and Chronic Lymphoid Leukaemia (CLL) remain at this time incurable diseases, with a very heterogeneous progression, and the diagnosis of which is sometimes very difficult.

SLE is a rare disease of autoimmune origin, characterized by the presence of autoreactive lymphocytes and of antinuclear autoantibodies (ANAs). It is a multisystemic disease with very varied clinical manifestations. The prevalence differs according to ethnic group, but is estimated at approximately 1 per 10 000, with a female/male ratio of 10:1. The clinical heterogeneity of this disease is a match for its etiopathogenic complexity, comprising at the same time genetic, epigenetic and environmental factors. SLE can affect all the organs. The most frequent manifestations are a rash, arthritis and fatigue. The most severe manifestations include kidney damage, neurological problems, cardiac problems, anaemia and thrombocytopenia. SLE is a disease which progresses through attacks, the diagnosis of which is difficult since it is necessary to combine several clinical and biological criteria in order to define an SLE (Petri M, Orbai A M, Alarcon G S, Gordon C, Merrill J T, Fortin P R, et al. Derivation and validation of the Systemic Lupus International Collaborating Clinics classification criteria for systemic lupus erythematosus. Arthritis Rheum. 2012; 64:2677-86, ([1])). The specificity of these criteria is imperfect and it is sometimes necessary to wait several years or decades for all of the criteria to be present, which can delay therapeutic treatment. More than 95% of patients present with ANAs which are considered to be positive about ⅟₁₆₀th. ANAs are not specific for SLE and the search for said ANAs must be supplemented with the demonstration of more specific autoantibodies, such as anti-DNA antibodies (30-70% depending on ethnic group and techniques used), anti-Sm antibodies (5-30%, depending on ethnic group), anti-ribosome antibodies (1-5%) and anti-PCNA (anti-Proliferating Cell Nuclear Antigen) antibodies (1%).

The current clinical objectives are to rapidly make the diagnosis of SLE, in order to treat the acute episodes, which can compromise the vital prognosis, and then to minimize the risks of attacks during periods of relative stability and to control the symptoms which, without placing the vital prognosis in danger, have repercussions on the daily quality of life. The activity of the disease is evaluated using clinical scores such as the "systemic lupus erythematosus disease activity index" which gives an account of the activity of the disease at a given moment (Bombardier C, Gladman D D, Urowitz M B, Caron D, Chang C H. Derivation of the SLEDAI, a disease activity index for lupus patients. The Committee on Prognosis Studies in SLE. Arthritis Rheum 1992; 35:630-40 ([2])). Hydroxychloroquine and non-steroidal anti-inflammatories are indicated in the moderate forms of SLE; corticoids and immunosuppressants are reserved for the more severe conditions; the anti-CD20 monoclonal antibody (Rituximab, Mabthera®) and the anti-BAFF antibody (Belimumab, Benlysta®) which target B lymphocytes (LBs) are currently indicated in more severely affected patients who have not responded to the usual treatments. Despite the improvement in the prognosis after the introduction of corticoids and immunosuppressants, SLE continues to have a significant impact on the morbidity-mortality of patients suffering therefrom.

CLL is a malignant and chronic hemopathy which also affects LBs. These cells play an important role in the immune system. During CLL, the CLL LBs are blocked in their life cycle, when they reach maturity, and their production continues. Consequently, these LBs end up accumulating in the blood, in the lymph nodes, the spleen, the liver and the bone marrow, which leads to an increase in volume of the secondary lymphoid organs. The current treatments available against CLL are most commonly used when the disease is at a progressed stage defined by clinicobiological criteria, such as the Binet score (Binet J L, Lepoprier M, Dighiero G, Charron D, D'Athis P, Vaugier G, Beral H M, Natali J C, Raphael M, Nizet B, Follezou J Y. A clinical staging system for chronic lymphocytic leukaemia: prognostic significance. Cancer. 1977; 40:855-64 ([3])), biological factors (Pflug N, Bahlo J, Shanafelt T D, Eichhorst B F, Bergmann M A, Elter T, et al. Development of a comprehensive prognostic index for patients with chronic lymphocytic leukaemia. Blood. 2014; 124:49-62, ([4])), and also the cytogenetic analysis of the cells (Novak U, Oppliger Leibundgut E, Hager J, Mühlematter D, Jotterand M, Besse C, Leupin N, Ratschiller D, Papp J, Kearsey G, Aebi S, Graber H, Jaggi R, Lüthi J M, Meyer-Monard S, Lathrop M, Tobler A, Fey M F. A high-resolution allelotype of B-cell chronic lymphocytic leukaemia (B-CLL). Blood. 2002; 100:1787-94, ([5])). The chemotherapy products used in the intensive treatment of CLL are chlorambucil used alone, fludarabine used alone, and monthly chemotherapy treatments of CHOP type (combination of four agents: Cyclophosphamide-(H)adryamycin-Oncovin(vincristine)-Prednisone). In terms of targeted therapy, since leukaemic LBs are CD20+, a monoclonal antibody which specifically recognizes this target can be used during treatment (rituximab, Mabthera®; ofatumumab, Arzerra®; and GA101, obinutuzumab). Another target is LB-specific Bruton's tyrosine kinase, the expression of which is increased in leukaemic cells. Ibrutinib, since it is an inhibitor of this enzyme, leads to the apoptosis (death) of leukaemic cells, allowing more prolonged remissions, even in the refractory or recurring forms. However, the treatments can expose patients to adverse effects.

In the pathology of SLE and of CLL, a disruption of the calcium signalling of LBs in SLE and CLL is described at rest and following stimulation of the LB antigen receptor (BCR) (Liossis S N, Kovacs B, Dennis G, Kammer G M, Tsokos G C. B cells from patients with systemic lupus erythematosus display abnormal antigen receptor-mediated early signal transduction events. J Clin Invest. 1996; 98:2549-57, ([6]); Dühren-von Minden M, Ubelhart R, Schneider D, Wossning T, Bach M P, Buchner M, et al. Chronic lymphocytic leukaemia is driven by antigen-independent cell-autonomous signalling. Nature. 2012; 489:309-12, ([7])).

The diagnosis of CLL and of SLE is thus based on a compilation of imperfect clinical and biological criteria, hence the need to develop new criteria for diagnosis and also for prognosis which are more effective than those that are known.

Furthermore, animal models for CLL are lacking or incompletely validated, several animal model exist for SLE and one of the most studied is related to the lupus prone mice model MRL/Lpr which reproduces most of the features of human SLE (Shlomchik, M. J., Madio, M. P., Ni, D., Trounstine, M. & Huszar, D. J. Exp. Med. 180, 1295-1306 (1994) [(10)]).

SUMMARY

It may therefore be beneficial to provide novel processes for the diagnosis of SLE and CLL, which address or overcome the defects, drawbacks and obstacles of the prior art.

Some embodiments makes it possible to satisfy these needs through the use of the STIM1 protein fraction located at the plasma membrane, STIM1 being a protein involved in calcium channel activation and regulation, as a biomarker in a process for the diagnosis of systemic lupus erythematosus (SLE) and/or of chronic lymphoid leukaemia (CLL).

Before the development of the embodiments, there were no predictive markers for the response to the treatment at that time for CLL and SLE. It is therefore in the context of significant and innovative research studies that the Applicant has succeeded in developing a novel process for the diagnosis and/or prognosis of CLL and/or of SLE. Advantageously, the process may be applied to the MRL/Lpr lupus prone mice model.

Some embodiments make it possible, in an entirely innovative manner, to use, in these pathological conditions, the variations in membrane STIM1 expression as a biomarker for the diagnosis and/or the prognosis of CLL and/or of SLE.

In the LBs and LTs (T lymphocytes) of lupus patients, and LBs from the MRL/Lpr lupus prone mice model, an increase in the overall expression of the STIM1 protein and an induction of the STIM1 fraction located at the plasma membrane, which remains low or even zero in human and murine control LBs and control LTs, are surprisingly observed in the context of the present invention. Thus, the invention proposes using the measurement of the expression of STIM1 in SLE as:

1) a diagnostic biomarker. The STIM1 expression level in LBs and LTs is a discriminating marker of SLE. The applicant has demonstrated the advantage of this marker for distinguishing lupus patients from other autoimmune pathological conditions (Goujerot-Sjogren syndrome and rheumatoid arthritis);

2) a prognostic biomarker. The applicant has demonstrated, in the context of the present invention, that there is an inverse link between the amount of membrane STIM1 in human and the activity of the lupus disease (SLEDAI score); and between the amount of membrane STIM1 in the murine lupus prone mice MRL/Lpr and proteinuria.

3) a therapeutic response biomarker.

In CLL LBs, the applicant has surprisingly demonstrated that two groups of patients can be distinguished according to the presence of the STIM1 protein in the membrane (group I) or its absence (group II). Also shown in the context of the present invention are an increase in total STIM1 expression and a defect of the methylation state of the STIM1 promoter for the CLL LBs of group I.

Thus, some embodiments propose using the measurement of STIM1 expression and/or the methylation state of the STIM1 promoter in CLL as:

1) a diagnostic biomarker. The STIM1 expression level is used as a diagnostic marker, in particular for the initial forms and the CLLs of which the Matutes score is at 3 (5% of CLLs);

2) a prognostic biomarker. The STIM1 expression level in LBs correlates with the clinical progression of the disease (Binet score);

3) a treatment response biomarker. The expression level of the membrane fraction of STIM1 and/or the methylation state of the STIM1 promoter are used, in the context of the invention, as a marker for the response to treatment and also to Rituximab (anti-CD20).

Some embodiments are advantageous in several respects, in particular due to the fact that the STIM1 protein located at the plasma membrane is present only on the affected cells, and not on the healthy cells, thereby enabling a gain in specificity and in selectivity. Furthermore, the expression, by immune cells, of the STIM1 protein at the plasma membrane facilitates its accessibility for a faster and easier diagnosis.

A first object of some of the embodiments thus relate to a process for the diagnosis of systemic lupus erythematosus (SLE) and/or of chronic lymphoid leukaemia (CLL) in a subject who may be suffering therefrom, comprising the in vitro detection of the expression of the fraction of the STIM1 protein located at the cell plasma membrane in a biological sample from the subject.

Another object of some of the embodiments relate to a process for predicting the progression and/or monitoring the progression of CLL and/or of SLE in a subject who may be suffering therefrom, comprising the in vitro detection of the expression of the fraction of the STIM1 protein located at the cell plasma membrane in a biological sample from the subject.

For the purposes of some of the embodiments, the term "biological sample" is intended to mean any tissue or cell from the subject, and derivatives thereof. It may come, for example, from a sample taken from the subject. It may, for example, be a blood sample, a bone marrow sample, or a sample from a lymph node biopsy.

For the purposes of some of the embodiments, the term "subject" is intended to mean any living human or animal being, for example an animal model. For example, the animal model may be a mouse. The subject may be a subject for whom it is desired to know whether they are suffering from the pathological condition. Alternatively, it may be a subject who is suffering from the pathological condition. In this case, it may be a subject undergoing treatment for the pathological condition, or following no treatment. The subject may also be a control subject. In this case, it may involve subjects suffering from the disease that it is desired to diagnose or monitor. In other embodiments, the control subject(s) correspond(s) to healthy patients, i.e. to individuals who are not suffering from the disease, described as "healthy".

For the purposes of some of the embodiments, the term "detection of the expression" is intended to mean any qualitative and/or quantitative identification of the expression or of the activity of the fraction of the STIM1 protein located at the cell plasma membrane. The detection may include a quantitative measurement of the expression or of the activity of the fraction of the STIM1 protein located at the cell plasma membrane. Alternatively, the detection may include a qualitative measurement of the expression or of the activity of the fraction of the STIM1 protein located at the cell plasma membrane, for example by means of a comparison of the expression detected for the subject analysed with a control subject, and/or a comparison with previously connected data which are available, for example, on a database.

The expression detected may be a presence or an amount of proteins, or any biological effect modulated by the use of a compound which targets the fraction of the STIM1 protein located at the plasma membrane, for example an effect on calcium fluxes, on cell survival, on autophagy, on cytokine production, on proliferation and on cell migration. The detection means used may be any means known to those skilled in the art, for example by quantification of messenger RNA, for example by quantitative RT-PCR and/or by hybridization techniques, for example using a labelled probe, or by using a DNA chip. In other embodiments, the methods according to the invention include the quantification of the fraction of the STIM1 protein located at the cell plasma membrane in the biological samples, for example through the use of an anti-STIM1 antibody, by flow cytometry, by Western blotting, by microscopy, by mass spectrometry, by immunoassay, in particular by ELISA. Also included are methods for testing the methylation state of the STIM1 promoter, for example the chromatin immunoprecipitation technique, methylation-sensitive PCR, the use of CpG chips, and also any study after treatment with sodium bisulfite.

In one particular embodiment, the detection of the fraction of the STIM1 protein located at the plasma membrane may also include detection of the various cell fractions of the STIM1 protein. The various cell fractions of STIM1 may be the fraction of the protein located at the plasma membrane and/or at the endoplasmic reticulum, or the total STIM1 fraction.

In one particular embodiment, the detection of the expression of the fraction of the STIM1 protein located at the plasma membrane is a measurement of the methylation state of the STIM1 promoter. The measurement of the methylation state of the STIM1 promoter can be carried out by any technique known to those skilled in the art. It may, for example, be the use of restriction enzymes sensitive or insensitive to DNA methylation, for instance MspI or HpaII, or the "Methylated DNA immunoprecipitation" technique with or without incubation with an anti-5-methylcytosine antibody. Advantageously, the methylation state of the membrane STIM1 promoter differs between subjects suffering from CLL or from SLE and healthy subjects not suffering therefrom. For example, a profile which is different from a control profile of a subject not suffering therefrom allows positive diagnosis of the disease, or the deduction of a weak response to a treatment of the disease, or the deduction of a progression of the disease.

For the purposes of some of the embodiments, the expression "fraction of the STIM1 protein located at the cell plasma membrane" is intended to mean the glycosylated fraction of the STIM1 protein located at the cell plasma membrane. The STIM1 protein has two glycosylation sites, one asparagine in position 131 and another in position 171. The glycosylation of the STIM1 molecule is a necessary and obligatory process for trafficking of the STIM1 molecule to the cell surface (Mignen O, Thompson J L, Shuttleworth T J. STIM1 regulates Ca2+ entry via arachidonate-regulated Ca2+-selective (ARC) channels without store depletion or translocation to the plasma membrane. J Physiol. (2007) 579:703-15, ([9])). This fraction has a molecular weight of approximately 90±2 kDa, which makes it possible to distinguish it from the non-glycosylated form of STIM1 (84±2 kDa). The two forms are detectable by the Western blotting technique. The human STIM1 molecule (Stromal Interacting Molecule; also known as GOK) is a protein of which the sequence SEQ ID NO. 1 corresponds to the Uniprot sequence: Q13586 or the NCBI sequence: NP_003147.2. This protein is encoded by the sequence SEQ ID NO. 2, corresponding to the NCBI sequence: NM_003156.3 (mRNA transcript). Preferably, the fraction is located on the plasma membrane of intact or entire cells, which means that the plasma membrane is non broken and/or non permeabilized, and advantageously does not allow non-permeant molecules to penetrate the cells.

The expression "fraction of the STIM1 protein located at the plasma membrane" is intended to mean any biological product resulting from the isolation of the STIM1 proteins located at the cell plasma membrane. The isolation can be carried out by any of the means known to those skilled in the art, for example by means of the use of a detergent (for example, a non-ionic or ionic surfactant such as Triton™ X-100 or Triton™ NI 01; or polyoxyethylene sorbitan esters), after differential centrifugation, or by means of an immunochemical or protein-chemical technique using a membrane-protein-targeting step (antibody, Thermo Scientific™ sulfo-NHS-SS-biotin), this list not being limiting.

For the purposes of some of the embodiments, the term "cell" is intended to mean any cell expressing STIM1 at the level of its plasma membrane. It may be an isolated cell or a set of cells such as a cell culture. The cells may be entire cells, in other word intact and/or non broken cells. Such cells are thus not permeabilized. Advantageously, the cells may be immune cells. They may, for example, be $L_B$s and $L_T$s, for example $L_B$s from subjects and mice for whom it is not known whether they are suffering from SLE or from CLL. In this context, they may be cells from subjects and mice suffering from SLE or from CLL, in particular before a treatment of the pathological condition, or during a treatment of the pathological condition, or after a treatment of the pathological condition; or alternatively from subjects who are healthy and/or not suffering from said pathological conditions. The cell used may be any cell endogenously or recombinantly expressing the fraction of the STIM1 protein located at the plasma membrane. By way of example, the cell may be a neuron or a primary neuron culture, for example a culture of spinal neurons. It may also be a host cell, such as Cos-7, CHO, BHK and HEK-293, stably or transiently expressing the fraction of the STIM1 protein located at the plasma membrane. The cells may be transfected with the sequence ID NO: 2 in order to express the STIM1 protein on their plasma membrane.

For the purposes of some of the embodiments, the term "process for the diagnosis" is intended to mean any process, which makes it possible to identify a subject suffering from SLE and/or from CLL and/or a subject not suffering from SLE and/or from CLL. The process of the invention is an in vitro process, i.e. it is carried out outside the subject for whom the diagnosis is desired. It is, for example, a test carried out on a biological sample from the subject to be diagnosed.

In the context of the diagnostic process of some of the embodiments, when the expression detected in the context of the process of the invention is an overexpression of the fraction of the STIM1 protein located at the cell plasma membrane compared with the level of expression of said fraction in a control cell from a subject not suffering from SLE or from CLL, this allows a positive diagnosis of SLE or of CLL to be made.

For the purposes of some of the embodiments, the term "overexpression" is intended to mean an expression that is quantitatively greater than that measured in a subject not suffering from SLE or from CLL. For example, the overexpression may be three times greater than the expression measured in a subject not suffering from said pathological conditions.

The diagnostic process of some of the embodiments may for example include steps consisting in:
(a) detecting or quantifying, in vitro, the expression and/or the activity of the fraction of the STIM1 protein located at the cell plasma membrane in a biological sample from the subject, and
(b) comparing the expression or the activity of the fraction of the STIM1 protein located at the cell plasma membrane obtained in step (a) with the expression or the activity of the fraction of the STIM1 protein located at the cell plasma membrane detected or quantified in one or more biological samples, from one or more control subjects, for example healthy subjects.

Advantageously, the subject or patient is diagnosed as suffering from the disease, or liable to be suffering therefrom, if their biological sample exhibits an expression or an activity for the fraction of the STIM1 protein located at the cell plasma membrane that is greater than that of the sample(s) from the healthy patients. On the other hand, if the activity or the expression of the fraction of the STIM1 protein located at the cell plasma membrane, determined in step (a), is less than or equal to that of the samples from the (healthy) control patients, then the diagnosis can be considered to be negative. It may be considered that the sample from the patient is positive if the sample exhibits an expression or an activity for the fraction of the STIM1 protein located at the cell plasma membrane that is at least 10% greater, preferably at least 20% greater, than that of the sample(s) from the healthy patients.

For the purposes of some of the embodiments, the term "prediction of the progression" is intended to mean any process which makes it possible to give a prognosis for the condition of the patient and/or the disease in the future. It may be a probability of progression of the disease and/or an evaluation of the possible outcome of the disease for a given period of time. It may be a short-term prediction, for example under three months to a year. The prediction may make it possible to evaluate the probability of the disease being in regression, being stationary or worsening within a predetermined period of time.

In one particular embodiment, the prediction of the progression may be carried out by correlation between the level of expression of the fraction of the STIM1 protein located at the cell plasma membrane and the clinical progression of the disease by calculation of the SLEDAI (Systemic Lupus Erythematosus disease activity index) score and/or proteinuria for SLE and of the Binet score for CLL.

The SLEDAI score can be calculated as mentioned in the document Bombardier et al. ([2]).

The Binet score can be calculated as mentioned in the document Binet et al. ([3]).

For example, when the level of expression of the fraction of the STIM1 protein located at the cell plasma membrane is less than ten times the value measured in a subject not suffering from the pathological condition, the clinical progression of the disease calculated by the SLEDAI score is favourable (negative predictive value).

For example, when the level of expression of the fraction of the STIM1 protein located at the cell plasma membrane is less than three times the value measured in a subject not suffering from the pathological condition, the clinical progression of the disease calculated by the Binet score is favourable (negative predictive value).

For the purposes of some of the embodiments, the term "monitoring the progression" is intended to mean any process for determining whether the disease is in regression, stationary or worsening. The monitoring of the progression can be carried out by comparing the expression of the fraction of the STIM1 protein located at the cell plasma membrane, detected at a given instant, with the expression of this fraction detected previously. The previous detection may be, for example, the detection on the day of the positive diagnosis of the disease. The monitoring of the progression can be carried out by means of at least two detections, and advantageously more than two detections, possibly carried out at regular intervals. When more than two detections are carried out, they can for example be every three months to one year.

The monitoring of the progression of the disease in a patient may include the steps consisting in:
(a) detecting or quantifying the activity or the expression of the fraction of the STIM1 protein located at the cell plasma membrane in a first biological sample, preferably of blood, taken from the patient at a time t1,
(b) detecting or quantifying the activity or the expression of the fraction of the STIM1 protein located at the cell plasma membrane in a second biological sample, preferably of blood, taken from the patient, the second sample having been taken at a time t2 after the time t1,
(c) comparing the expression or the activity of the fraction of the STIM1 protein located at the cell plasma membrane of step (b) with that determined in step (a).

The comparison of the expression or of the activity of the fraction of the STIM1 protein located at the cell plasma membrane in step (c) is a criterion which makes it possible to determine the progression or the stage of the disease. It is thus possible to determine whether the disease is in regression, stationary or worsening.

If the sample of step (b) exhibits a level of expression of the fraction of the STIM1 protein located at the cell plasma membrane that is less than the expression or than the activity determined in step (a), it can be concluded that the disease is in regression. Conversely, if the sample of step (b) exhibits an expression or an activity of the fraction of the STIM1 protein located at the cell plasma membrane that is greater than that measured in the first step, the disease is progressing.

Advantageously, the progression can be monitored in response to a therapeutic treatment in human and mice. In this context, the monitoring can be carried out by detecting, in vitro, the expression of the fraction of the STIM1 protein located at the cell plasma membrane at various moments of the treatment, and by comparing the data obtained by means of the detection with a control value, possibly obtained in the same subject, for example before the beginning of the treatment, or in a subject not suffering from the pathological condition. For example, the monitoring can be carried out approximately every month, or approximately every two months, or approximately every three months, or approximately every six months, starting from the day on which the treatment is started. Advantageously, the comparison of the results obtained throughout the monitoring may make it possible to identify a decrease in the progression of the pathological condition in response to the treatment, and/or a slowing down or a blocking of the development of the disease and/or the fact that one or more symptoms of the disease have been relieved, reduced or slowed down, or else the fact that said disease has been cured.

In this embodiment, the in vitro evaluation of the efficacy of a therapeutic treatment of the disease may include the steps consisting in:

(a) detecting or quantifying the expression or the activity of the fraction of the STIM1 protein located at the cell plasma membrane in a biological sample of a subject, for example from a patient before treatment, (b) detecting or quantifying the expression or the activity of the fraction of the STIM1 protein located at the cell plasma membrane in a biological sample of a subject, for example from the patient after treatment, (c) comparing the expression or the activity of the fraction of the STIM1 protein located at the cell plasma membrane of step (a) with that determined in step (b).

The efficacy of the treatment can be determined by comparing the expressions of the fraction of the STIM1 protein located at the cell plasma membrane in the samples (a) and (b). If the expression or the activity of the fraction of the STIM1 protein located at the cell plasma membrane is lower in the sample of step (b) than in the sample of step (a), this means that the treatment is effective. If there is an increase in the expression of the fraction of the STIM1 protein located at the cell plasma membrane, it may be considered that the treatment is barely active or is inactive depending on the size of the variation observed. In certain embodiments, it is considered that the treatment has a therapeutic effect on the disease if it involves a decrease in expression or in activity of the fraction of the STIM1 protein located at the cell plasma membrane of at least 10%, preferably of at least 20%. The biological samples, taken before treatment and after treatment, are preferably blood samples.

The therapeutic treatment may also include a substance which interacts with said fraction. The substance may be any molecule which interacts with the fraction of the STIM1 protein located at the cell plasma membrane. The interaction may be of the type such as binding of the candidate molecule to the STIM1 protein located at the cell plasma membrane. Alternatively, the interaction may be a modulation of the activity or of the expression of this protein. The modulation of the activity of the fraction of the STIM1 protein located at the plasma membrane may be due to a modification of the insertion of STIM1 into the plasma membrane, or to a modification of its interaction with the proteins which are associated therewith. The modulation of the activity of the protein can result in a modification of calcium fluxes, such as a modification of the constitutive entry of intracellular calcium or a modification of calcium entry activated during the stimulation of a receptor, such as store operated calcium entry (SOCE). The modulation of expression may be an increase or a decrease in the expression of the STIM1 protein located at the plasma membrane compared with a level measured on the same cell or on a comparable cell before application of the candidate molecule. The modulation of the expression of the STIM1 protein may, for example, be linked to transcriptional modifications, epigenetic modifications or a modulation of the glycosylation process essential for membrane trafficking of the STIM1 protein.

The substance may be of natural or synthetic origin. It may be a protein produced chemically or by any biological engineering process, for instance a purification. The substance may, for example, be an antibody directed against an extracellular fragment of the STIM1 protein located at the plasma membrane, of sequence SEQ ID NO. 3. This sequence may correspond to the amino acids between positions 23-213 of STIM1. It may be the anti-GOK/STIM-1 antibody (Clone: 44, BD Biosciences reference 910954).

The treatment may also include any active ingredient which potentiates the effect of the substance as defined above. It may also be an anti-CD20 antibody or any other molecule associated with the protein complex which regulates STIM1-protein-associated calcium channels, such as the Orai and TRPC proteins. In this case, it may be any anti-CD20 known in human or animal therapy, for example the IDEC-C2B8 antibody (Rituximab, distributed by Hoffman-la Roche in Europe, Drugbank DB00073 (BIOD00014, BTD00014)), ofatumumab (AZERRA®, Glaxo-Smith-Kline), tositumomab (GSK, DB00081, BIOD00085, BTD00085), obinutuzumab (GAZYVA®, Roche, DB08935, GA101), ibritumomab (Tiuxetan, IDEC Pharmaceuticals, DB00078, BIOD00069, BTD00069), ublituximab (LFB) or AME-133v (Lilly, LY2469298), this list not being limiting.

Another subject of some of the embodiments relate to the use of a substance which interacts with the fraction of the STIM1 protein located at the cell plasma membrane, for detecting, predicting the progression of, monitoring the progression of and/or evaluating, in vitro, the efficacy of a medicament for the treatment of CLL and/or SLE.

Advantageously, the substance which interacts with the fraction of the STIM1 protein located at the cell plasma membrane does not penetrate into the cells and stays at the plasma membrane, due to its specific interaction with the fraction of the STIM1 protein localized to the plasma membrane. In other words, the substance may be a non permeant molecule, i.e. molecule that does not cross the plasma membrane. Advantageously, as the substance does not cross the plasma membrane, it does not interact with the STIM1 protein localized to the endoplasmic reticulum.

EXAMPLES

Figure 1:
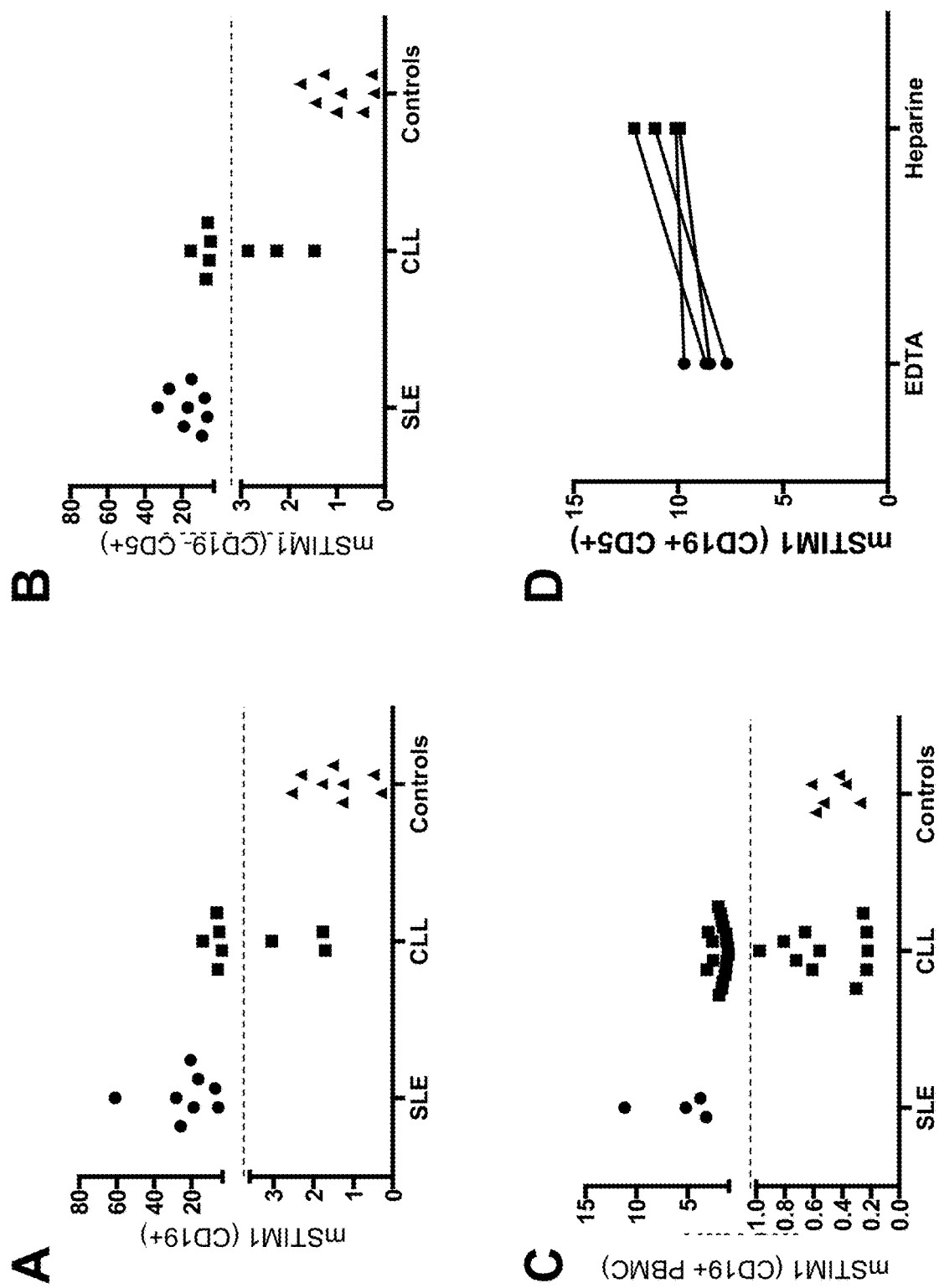
FIG. 1 shows the measurement of the expression of STIM1 at the membrane surface (mSTIM1 or membrane STIM1) of B and T lymphocytes during SLE or CLL or in healthy controls, by flow cytometry. The mean fluorescence intensities (IMF) are indicated for each condition (whole blood and PBMCs) as are the values retained for defining the positivity threshold (mean+/−3 standard deviations of the negative controls, hatched line). This measurement was carried out on whole blood with B lymphocytes (CD19+, A) being distinguished from T lymphocytes (CD19-, CD5+, B), and also on B cells (CD19+) after purification of PBMCs (peripheral blood mononuclear cells, C). The nature of the anticoagulant (EDTA or lithium heparinate) used during the taking of the blood sample does not interfere with the measurement of the expression of STIM1 at the membrane surface of the B lymphocytes (4 CLLs positive for membrane STIM1 were tested) (D).

Example 1: Process for Demonstrating Membrane STIM1

B Lymphocytes were Purified from Peripheral Blood Mononuclear Cells (PBMCs) obtained on a Ficoll® gradient after removal of the T lymphocytes (rosette technique using sheep red blood cells pretreated with neuraminidase) and of the monocytes (negative depletion technique, B cell kit without CD43, STEMCELL TECHNOLOGIES™). The purity of the CD19-positive $L_B$s was verified by flow cytometry showing a purity greater than 95%.

A/B—Protein analysis of the $L_B$s by Western blotting on SDS-PAGE made it possible to distinguish, in addition to the reticular fraction of STIM1 (84±2 kDa), the membrane and glycosylated form of STIM1 (90±2 kDa) for the SLE $L_B$s (A) and for certain CLL diseases (B, mSTIM1+ group). This protein analysis first of all used an anti-STIM1 antibody, clone Gok/44 (BD Biosciences), then a peroxidase-coupled anti-mouse IgG antibody (GE Healthcare), and finally revealing by chimioluminescence (ECL advance kit, GE Healthcare).

C/D—The flow cytometry analysis consisted in incubating the purified LBs with an anti-STIM1 antibody, clone Gok/44 (BD Biosciences) for 15 min at 4° C., then, after washing, the binding of the anti-STIM1 antibody was revealed using a fluorescein-coupled anti-mouse IgG F(ab')2 antibody (Jackson laboratories). The membrane labelling of STIM1 in the living cells is determined with respect to the isotype control (IgG2a, Beckman Coulter).

Example 2: Study of Membrane STIM1 Expression by Flow Cytometry

The labelling consists in using an anti-STIM1 monoclonal antibody (mAb) (clone GOK/44, BD Biosciences, reference 610954). This mAb can be coupled, for example, with phycoerythrin (PE), which makes it possible to use it in combination with other labelled mAbs, for instance in human the anti-CD19 mAb coupled to Krome Orange™ (clone J3-119, Beckman Coulter, reference A96418), and also the anti-CD5 mAb coupled to APC-AF700 (clone BI1a, Beckman Coulter, reference A78835); and in mice the anti-B220 mAb coupled to APC-AF700 (clone RA3-6B2, Biolegend®, reference 10323(1/2)), the anti-CD5 mAb coupled to Cy5.5 (clone 53-7.3, Biolegend®, reference 10062(3/4)), and also the anti-IgM mAb coupled with fluoresceine (clone RMN-1, Biolegend®, reference 40650(5/6)). In the absence of coupling, the anti-STIM1 mAb can be revealed with a fluorescein-coupled anti-IgG mAb (anti-IgG F(ab')2, Dako®, reference F0479).

After 10-15 minutes of labelling (Table 1), the cells are washed and then analysed by flow cytometry (Navios 10 colours system and FC500 5 colours system, Beckman Coulter). The analysis of the membrane STIM1 labelling can then be carried out on the lymphocytes, which are distinguished according to the size and the structure of the cells by flow cytometry, or according to the other markers selected, for example B lymphocytes (CD19+) and T lymphocytes (CD19− CD5+) in human, and immature/naïve B cells (B220low IgM+) and mature B cells (B220high IgM+) in mice.

The different variants concern: (1) the use of whole blood with the need to use a red blood cell lysis step (VerssaLyse™ lysing solution, Beckman Coulter, ref A09777), (2) the use of PBMCs (peripheral blood mononuclear cells) after purification of the cells on a Ficoll-Hypaque® density gradient (d=1.077), and, finally, (3) the purification of the B lymphocytes by depletion (B cell separation kit, Miltenyi, Bergisch Gladback, Germany) or by the rosette technique using sheep red blood cells treated with neuraminidase, on PBMCs (Tak Yan Yu D. Lymphocyte subpopulations. Human red blood cell rosettes. Clin Exp Immunol. 1975, ([8])).

TABLE 1

Study of the membrane expression of STIM1 at the surface of lymphocytes in human and mice according to various experimental protocols.

|  | Human | | | Mice |
| --- | --- | --- | --- | --- |
|  | Whole blood | PBMCs | Purified B cells | Whole blood |
| Blood (EDTA, Heparin) | 50 µl | 15 ml | 15 ml | 50 µl |
| PBS | no | 15 ml | 15 ml | no |
| Ficoll-hypaque | no | 15 ml | 15 ml | no |
| Centrifugation (time) | no | 430 g (5 min) | 430 g (30 min) | no |
| B cell purification | no | no | yes | no |
| Cells/tubes | no | 500 000 | 500 000 | no |
| Coupled anti-STIM1 | yes | yes | no | yes |
| Coupled anti-hCD5 | yes | yes | no | |
| Coupled anti-hCD19 | yes | yes | no | |
| Coupled anti-mCD5 | no | no | no | yes |
| Coupled anti-mIgM | no | no | no | yes |
| Coupled anti-B220 | no | no | no | yes |
| Non-coupled anti-STIM1 | no | no | yes | no |
| Incubation | 10 min, RT | 30 min, 4° C. | 30 min, 4° C. | 20 min, RT |
| Washing (PBS) | — | — | 2 × 2 ml | — |
| Centrifugation (time) | — | — | 430 g (10 min) | — |
| Coupled anti-IgG | — | — | 3 µl | — |
| Incubation | — | — | 30 min, 4° C. | — |
| Washing (PBS) | 2 × 2 ml | 2 × 2 ml | 2 × 2 ml | 2 × 2 ml |
| Centrifugation (time) | 430 g (10 min) | 430 g (10 min) | 430 g (10 min) | 430 g (10 min) |
| Red cell lysis | yes | no | no | yes |

Abbreviations: RT: room temperature; PBS: phosphate buffered saline solution; PBMCs: peripheral blood mononuclear cells; h: human; m: mice.

This protocol was carried out in the context of the measurements relating to FIG. 1. Table 2a shows the measurement of the expression of STIM1 at the membrane surface of lymphocytes during systemic lupus erythematosus (SLE) and chronic lymphoid leukaemia (CLL) and also in healthy controls, by flow cytometry. For each condition, the mean fluorescence intensity (MFI) is indicated, as are the minimum value, the maximum value, and the number of samples analysed, which are indicated between brackets (min-max; and number of patients tested). Table 3a shows that the measurement of the positivity threshold for STIM1 at the membrane surface of the lymphocytes is calculated from the values obtained with the healthy controls (mean+/−3 standard deviations of the negative controls). This threshold value makes it possible to distinguish the positive patients suffering from systemic lupus erythematosus (SLE) and from chronic lymphoid leukaemia (CLL) with respect to the negative healthy controls, thus making it possible to calculate the percentage positivity. Table 2b/3b: similar to Tables 2a/3a except that measurement was performed in lupus prone mice MRL/Lpr and in the control C57Bl/6 mice.

TABLE 2a

| | human | | |
|---|---|---|---|
| | SLE | CLL | Healthy controls |
| B cells | | | |
| Blood | 23.1 (5.9-61; n = 8) | 5.3 (1.7-14.1; n = 8) | 1.5 (0.3-2.6; n = 8) |
| PBMCs | — | 1.7 (0.1-2.0; n = 6) | 0.5 (0.2-0.6; n = 6) |
| Purified B cells | 5.8 (3.2-11.2; n = 4) | 1.3 (0.2-3.1, n = 30) | 0.5 (0.3-0.6; n = 6) |
| T cells | | | |
| Blood | 16.8 (6.5-19.1; n = 8) | 5.7 (1.5-15.4; n = 8) | 0.9 (0.5-1.5; n = 8) |

TABLE 2b

| | mice | | | |
|---|---|---|---|---|
| | MRL/Lpr (lupus mice) | | C57BL/6 (control mice) | |
| B cells | Week 9 (no disease) | Week 19 (active disease) | Week 9 | Week 19 |
| Naïve | 1.2 (1-1.5 n = 4) | 18.6 (1.5-53 n = 7) | 1 (1-1.1 n = 4) | 1.7 (1.5-2 n = 5) |
| Mature | 1.2 (1-1.6 n = 4) | 4 (1-19.4 n = 7) | 1 (1-1.1 n = 4) | 1.6 (1.5-1.8 n = 5) |

TABLE 3a

| | in human | | |
|---|---|---|---|
| | Positivity threshold | SLE | CLL |
| B cells | | | |
| Blood | 3.6 | 8/8 (100%) | 5/8 (62.5%) |
| PBMCs | 1 | — | 2/4 (66.6%) |
| Purified B cells | 1 | 4/4 (100%) | 18/30 (60%) |
| T cells | | | |
| Blood | 3 | 8/8 (100%) | 5/8 (62.5%) |

TABLE 3b

| | in mice | | | |
|---|---|---|---|---|
| | | MRL/Lpr (lupus mice) | | C57BL/6 (control mice) |
| B cells | Positivity threshold | Week 9 (no disease) | Week 19 (active disease) | Week 9 | Week 19 |
| Naïve | 3.5 | 0/4 (0%) | 4/7 (57%) | 0/4 (0%) | 0/5 (0%) |
| Mature | 3.0 | 0/4 (0%) | 2/7 (29%) | 0/4 (0%) | 0/5 (0%) |

Example 3: Measurement of the Total STIM1 Expression

Total STIM1 expression was measured after permeabilization of the cells in order to measure the various STIM1 fractions contained at the plasma membrane and also at the endoplasmic reticulum membrane. In practice, the analysis is carried out on 500 000 LBs previously purified and fixed (4% paraformaldehyde in phosphate buffered saline (PBS), 10 min at 4° C.) and then permeabilized (0.1% of saponin in a solution of PBS-BSA (bovine serum albumin) 1%, 10 min at 4° C.). The labelling consists in using an anti-STIM1 mAb (clone GOK, BD Biosciences) revealed using a fluorescein-coupled anti-mouse IgG antibody (anti-IgG F(ab')2, Dako®, ref F0479).

Figure 2:
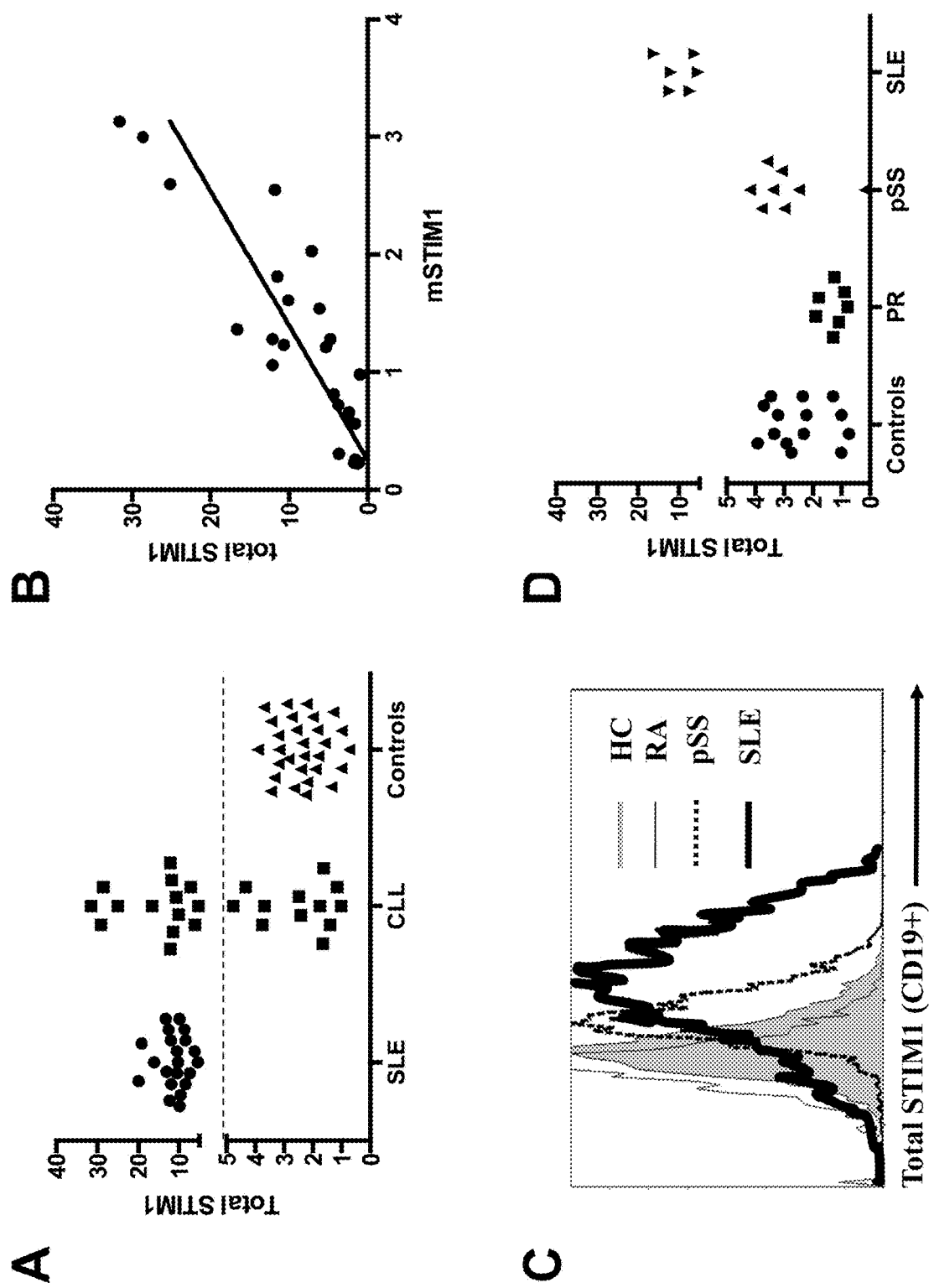
FIG. 2 shows that the surface expression of STIM1 in the B lymphocytes correlates with the labelling of all the STIM1 fractions (plasma membrane and endoplasmic reticulum, total STIM1). In practice, the analysis is carried out on 500 000 B lymphocytes previously purified and fixed (4% of a solution of paraformaldehyde in PBS (phosphate buffered saline), 10 min at 4° C.) and then permeabilized (0.1% of a solution of saponin in PBS-1% BSA, 10 min at 4° C.). The labelling consists in using an anti-STIM1 monoclonal antibody (mAb) (clone GOK/44, BD Biosciences, ref 610954) revealed with a fluorescein-coupled anti-mouse IgG antibody (anti-IgG (F(ab')2 (Dako®, ref F0479)). A—The measurement of the expression of total STIM1 on purified and permeabilized B lymphocytes isolated from the peripheral blood of patients having systemic lupus erythematosus (SLE, n=21) or chronic lymphoid leukaemia (CLL, n=26) or from healthy controls (n=29). The value of 5.0 retained for defining the positivity threshold (mean+/−3 standard deviations of the negative controls) is indicated by a hatched line. B— Shows the strong correlation between the measurement of membrane STIM1 (x-axis) and of total STIM1 (y-axis) carried out on permeabilized cells (Pearson correlation test $r^2=0.76$, $P<10^{-4}$). C/D—The increase in STIM1 observed during SLE is not observed in other autoimmune pathological conditions such as rheumatoid arthritis (RA, n=7) and primary Gougerot Sjögren syndrome (pSS, n=8); a representative example for each pathological condition is represented and can be compared to Healthy Control (HC) (C).

This protocol was carried out in the context of the measurements relating to FIG. 2.

Table 4 shows the measurement of the positivity threshold for total STIM1 calculated from the values obtained with the healthy controls (mean+/−3 standard deviations of the negative controls). This threshold value (5.0 in the example) makes it possible to distinguish the positive patients suffering from systemic lupus erythematosus (SLE) and from chronic lymphoid leukaemia (CLL) with respect to the negative patients, thus making it possible to calculate the percentage positivity.

TABLE 4

|  | SLE | CLL | Healthy controls |
|---|---|---|---|
| Purified B cells | 11.2 (6.2-19.2; n = 21) | 9.5 (1.0-31.6; n = 26) | 2.4 (0.7-3.9; n = 29) |
| Positivity threshold | — | — | 5.0 |
| Positive/negative (%) | 0/21 (100%) | 12/26 (46.1%) | 0/29 (0%) |

Example 4: Determination of the Methylation State of the STIM1 Promoter

The genomic DNA is extracted from the previously purified B lymphocytes (Biosprint 15 DNA blood kit, Qiagen), and then quantified (Nanodrop™ 2000c, Thermo Scientific™). The Daudi (ATCC CCL-213) and Ramos (ATCC CRL-1596) human lines are used as B lymphocyte controls. Two techniques (3a and 3b) are used to determine the methylation state of the DNA of the STIM1 promoter.

Technique 3a: this first technique is based on the use of restriction enzymes such as HpaII which is sensitive to the methylation state of CpG motifs within CCGG motifs, and MspI which is insensitive to the methylation state of CpG motifs. In practice, 200 ng of DNA are incubated in the presence of the buffer alone, of the HpaII enzyme (10 units, New England Biolabs®, ref r0171), or of the MspI enzyme (10 units, New England Biolabs®, ref R0106) for 12 h at 37° C.

Technique 3b: this second technique requires a first step of DNA fragmentation (dsDNA Sherase, 20 min at 42° C. then 5 min at 65° C. in order to inactivate the enzyme, Zymo Research, Ref E2018). The DNA fragments are then incubated in the presence of anti-5-methylcytosine antibody and of protein A (Methylated-DNA immunoprecipitation (IP) kit, Zymo Research, ref D5101). Finally, the DNA/Antibody/Protein A complexes are isolated and then the antibody is inactivated (75° C., 5 min).

Technique 3c (this step is common to techniques 3a and 3b): the target regions are amplified by genomic PCR (polymerase chain reaction). The PCR cycles retained for the amplification are the following: first of all, an initial denaturation step (95° C., 5 min), then 35 cycles comprising a denaturation phase (95° C., 30 sec), a hybridization phase (60° C., 30 sec), and also an elongation phase (72° C., 1 min), and, finally, a final elongation step (72° C., 5 min).

Reading for technique 3a+3c: the amplification of the HpaII tube is compared with the tube without enzyme (100% methylation) and also with the MspI tube (0% methylation).

Reading for technique 3b+3c: the amplification of the methylated-DNA IP tube provides information about the methylation state of the zone captured by the anti-5-methylcytosine antibody. The amplification of the methylated-DNA IP tube is compared with the tube without IP (100% methylation).

Figure 3:
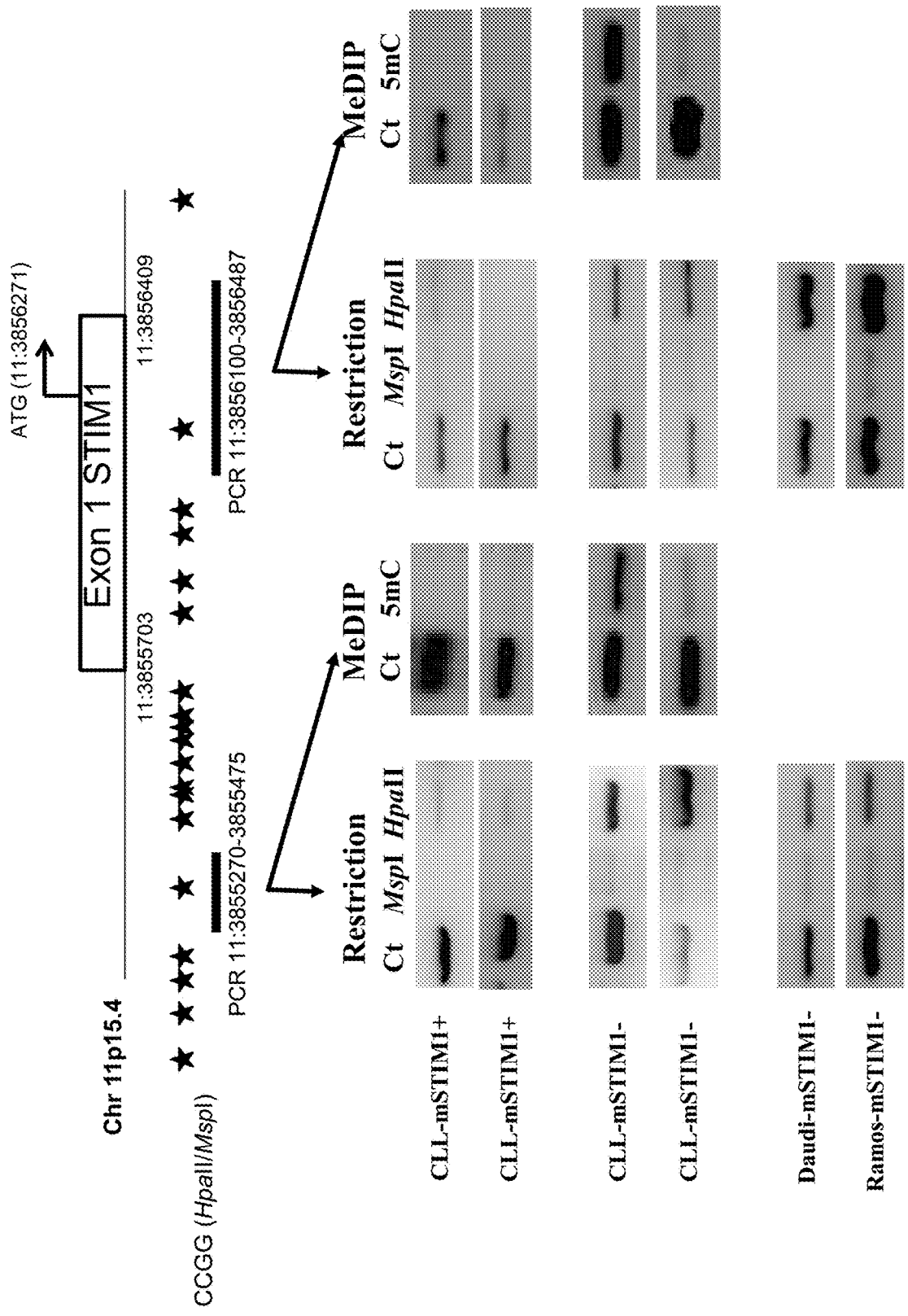
FIG. 3 shows that the methylation status of the STIM1 promoter provides information about the level of expression of STIM1 at the surface of the plasma membrane. The level of methylation of the DNA of the STIM1 gene (chromosome 11p15.4) at the level of its promoter and of its first exon by means of two different techniques (use of DNA methylation-sensitive or -insensitive restriction enzymes MspI or HpaII, and a control group Ct without restriction enzyme; and use of the "Methylated DNA immunoprecipitation" or MeD-IP technique) on a control group Ct (sample before incubation with an anti-5-methylcytosine antibody and then immunoprecipitation) or a 5mC group (sample incubated in the presence of anti-5-methylcytosine antibody and then immunoprecipitated) differs between the patients who are positive for membrane STIM1 (CLL mSTIM1+) with respect to the patients who are negative for membrane STIM1 (CLL mSTIM1−) and also with respect to the control human B lines (Daudi and Ramos mSTIM1− lines).

The results are shown in FIG. 3.

TABLE 5

Selection of the primers for the study of the methylation state of the STIM1 promoter. Two pairs of primers were selected so as to frame a CCGG site and 18 CpG sites located in the promoter of exon 1 of the STIM1 gene (Chromosome 11: 3855270-3855475, 206 bp amplicon), and to frame a CCGG site and 16 CG sites located in exon 1 of the STIM1 gene (Chromosome 11: 3856100-3856487, 388 bp amplicon).

| Position | Forward primer | Reverse primer |
|---|---|---|
| Chr 11: 3855270-3855475 | 5'-TCTAGAACTGAGGCGAGTGGA-3'<br>SEQ ID NO: 4 | 5'-GCGCTAGTCTTTGCCAGGAT-3'<br>SEQ ID NO: 5 |
| Chr 11: 3856100-3856487 | 5'-AGCACTTGACCTTTGGCTGT-3'<br>SEQ ID NO: 6 | 5'-ATTTCAACTTGCCCACTTCG-3'<br>SEQ ID NO: 7 |

Figure 4:
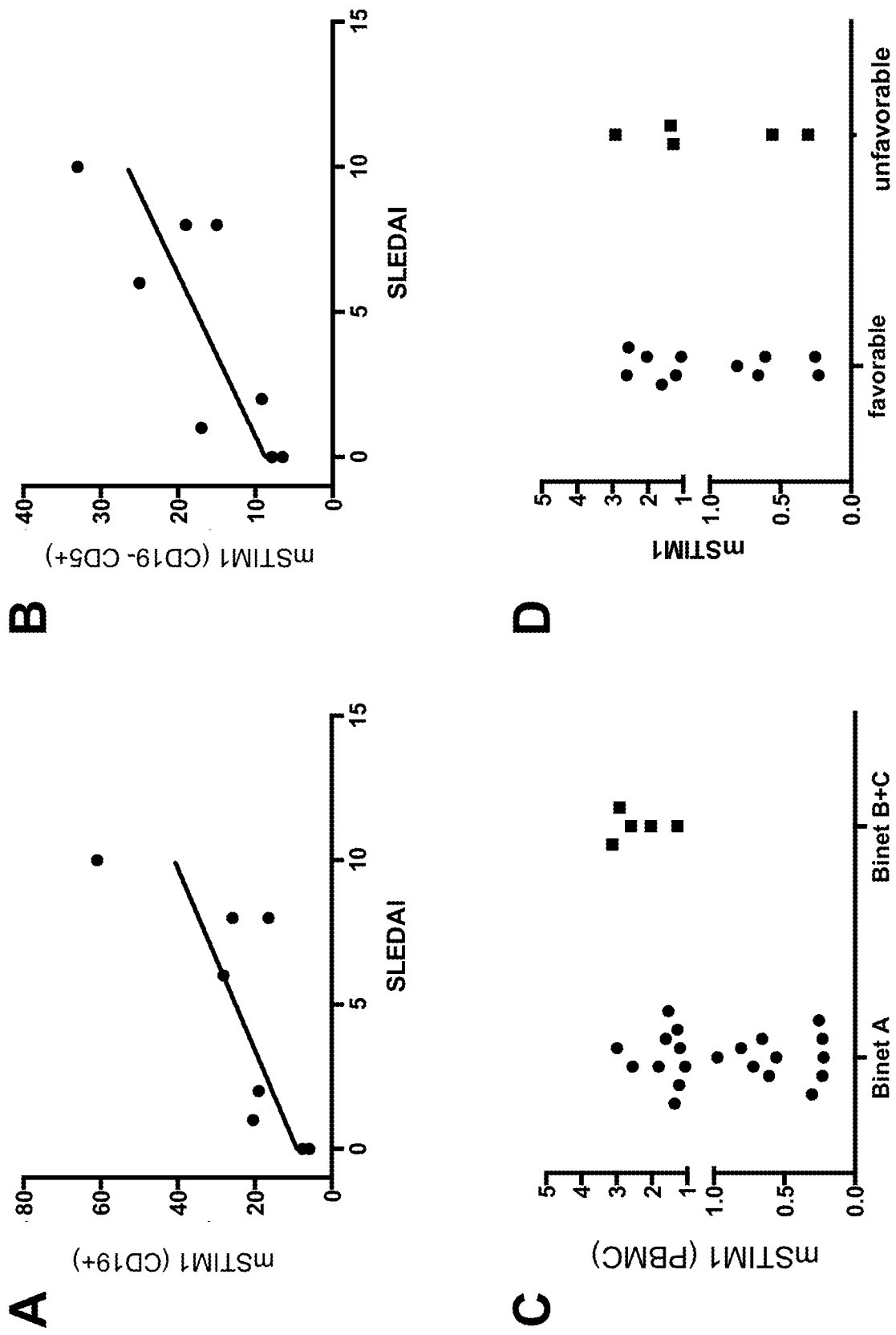
FIG. 4 shows that the measurement of STIM1 at the surface of the plasma membrane provides information about the state of activity of the disease. A/B: during systemic lupus erythematosus (SLE), the values of STIM1 at the surface of the plasma membrane (mSTIM1) of the B lymphocytes (A) and T lymphocytes (B) in whole blood correlate (Pearson correlation test $r^2=0.57$ and $r^2=0.64$, $P=0.03$ and $P=0.01$ respectively) with the SLEDAI (SLE disease activity index, ref 2) score. C— During chronic lymphoid leukaemia (CLL), for the patients with a poor prognosis (Binet stage B and C, reference 3, left-hand graph), the presence of STIM1 at the plasma membrane is noted, and (D) this effect appears to be independent of the cytogenetic status (favourable cytogenetic status: normal karyotype, and isolated 13q14 deletion, versus unfavourable cytogenetic status: 11q/ATM deletions, and 17p/TP52 deletions, reference 4, right-hand graph).
Figure 5:
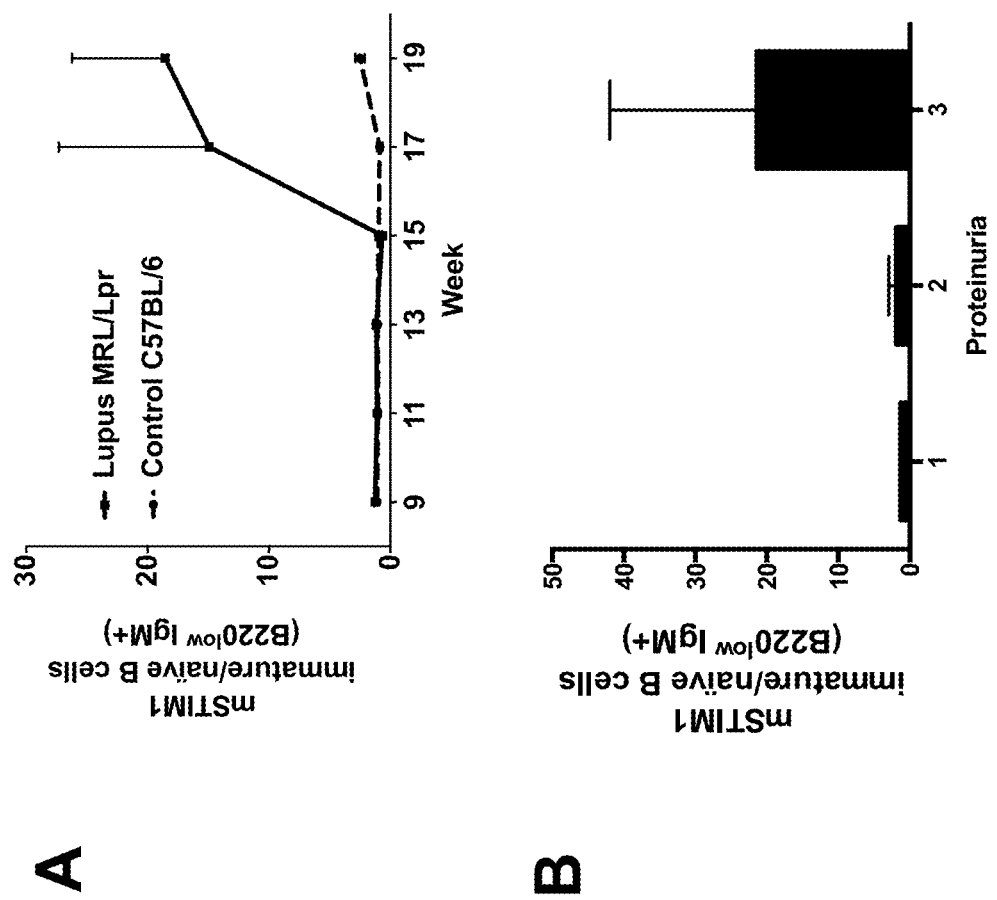
FIG. 5 shows that the peripheral blood surface expression of STIM1 in the immature/naïve B cell subset of lupus prone mice MRL/Lpr correlates with proteinuria. In practice, MRL/Lpr lupus prone mice (n=7) and C57BL/6 control mice (n=5) were selected and the measurement of STIM1 at the membrane surface of immature/naïve B cells (B220$^{low}$ CD19$^+$ IgM$^+$) was performed from week 9 (asymptomatic disease in MRL/Lpr mice) to week 19 (renal disease in MRL/Lpr mice). A—kinetic of plasma membrane STIM1 apparition in immature/naïve B cells from MRL/Lpr lupus prone mice and C57BL/6 control mice. C— An elevated level of STIM1 at the plasma membrane of immature/naïve B cells from MRL/Lpr mice is associated with proteinuria (measured by dipstick on a 0-4 scale; Urine Multistix® 8SG, Siemens).

Example 5: Measurement of STIM1 at the Surface of the Plasma Membrane Provides Information about the State of Activity of the Disease The measurement of STIM1 at the surface of the plasma membrane provides information about the state of activity of the disease, as is illustrated in FIG. 4. Table 6 shows that the absence of STIM1 molecule at the surface of the plasma membrane (mSTIM1) provides information about the in vivo therapeutic response using an anti-CD20 monoclonal antibody in a patient suffering from CLL.

TABLE 6

| Patient | Age | Sex | Binet | Cytogenetic | Treatment | Response | Relapse | mSTIM1 |
|---|---|---|---|---|---|---|---|---|
| CLL-1 | 77 | M | B | 13q14 | Anti-CD20 | Partial | Yes (3 months) | Yes |
| CLL-2 | 47 | M | C | Unknown | Anti-CD20 | Partial | Unknown | Yes |
| CLL-3 | 60 | M | C | 11q/ATM, 13q14 | Anti-CD20 | Partial | Yes (<1 year) | Yes |
| CLL-4 | 71 | F | B | 17p/TP52, 13q14 | Anti-CD20 | Complete | Yes (>2 years) | No |

LIST OF REFERENCES

1—Petri M, Orbai A M, Alarcon G S, Gordon C, Merrill J T, Fortin P R, et al. Derivation and validation of the Systemic Lupus International Collaborating Clinics classification criteria for systemic lupus erythematosus. Arthritis Rheum. 2012; 64:2677-86.

2—Bombardier C, Gladman D D, Urowitz M B, Caron D, Chang C H. Derivation of the SLEDAI. A disease activity index for lupus patients. The Committee on Prognosis Studies in SLE. Arthritis Rheum 1992; 35:630-40.

3—Binet J L, Lepoprier M, Dighiero G, Charron D, D'Athis P, Vaugier G, Beral H M, Natali J C, Raphael M, Nizet B, Follezou J Y. A clinical staging system for chronic lymphocytic leukaemia: prognostic significance. Cancer. 1977; 40:855-64.

4—Pflug N, Bahlo J, Shanafelt T D, Eichhorst B F, Bergmann M A, Elter T, et al. Development of a comprehensive prognostic index for patients with chronic lymphocytic leukaemia. Blood. 2014; 124:49-62.

5—Novak U, Oppliger Leibundgut E, Hager J, Mühlematter D, Jotterand M, Besse C, Leupin N, Ratschiller D, Papp J, Kearsey G, Aebi S, Graber H, Jaggi R, Lüthi J M, Meyer-Monard S, Lathrop M, Tobler A, Fey M F. A high-resolution allelotype of B-cell chronic lymphocytic leukaemia (B-CLL). Blood. 2002; 100:1787-94.

6—Liossis S N, Kovacs B, Dennis G, Kammer G M, Tsokos G C. B cells from patients with systemic lupus erythematosus display abnormal antigen receptor-mediated early signal transduction events. J Clin Invest. 1996; 98:2549-57.

7—Dühren-von Minden M, Ubelhart R, Schneider D, Wossning T, Bach M P, Buchner M, et al. Chronic lymphocytic leukaemia is driven by antigen-independent cell-autonomous signalling. Nature. 2012; 489:309-12.

8—Tak Yan Yu D. Lymphocyte subpopulations. Human red blood cell rosettes. Clin Exp Immunol. 1975.

9. Mignen O, Thompson J L, Shuttleworth T J. STIM1 regulates Ca2+ entry via arachidonate-regulated Ca2+-selective (ARC) channels without store depletion or translocation to the plasma membrane. J Physiol. (2007) 579:703-15.

10. Shlomchik, M. J., Madio, M. P., Ni, D., Trounstine, M. & Huszar, D. J. Exp. Med. 180, 1295-1306 (1994)

The invention claimed is:

1. A method for determining if a human patient suffering from systemic lupus erythematosus (SLE) is at risk for disease progression, said method comprising:
   (a) providing a sample comprising B cells from the patient;
   (b) measuring the level of expression of stromal interaction molecule 1 (STIM1) comprising SEQ ID NO: 1 at the plasma membrane surface of the B cells of the sample;
   (c) comparing the measured level of expression of STIM1 to the level of expression of STIM1 expressed on the surface of B cells of a human subject not suffering from SLE; and
   (d) determining that the patient is at risk for disease progression if the measured level of expression of STIM1 is greater than the level of expression of STIM1 expressed on the surface of B cells of a human subject not suffering from SLE.

2. The method of claim 1, wherein the level of expression of STIM1 at the plasma membrane surface of the B cells is measured using an immunoassay.

3. The method of claim 2, wherein the immunoassay comprises the use of flow cytometry, microscopy, or an ELISA.

4. The method of claim 2, wherein the B cells from the patient are contacted with an antibody that specifically binds to STIM1.

5. The method of claim 4, wherein that antibody that specifically binds to STIM1 binds to a polypeptide comprising SEQ ID NO: 3.

6. The method of claim 2, wherein the B cells from the patient are contacted with an antibody that specifically binds to CD19 or CD20.

7. The method of claim 1, wherein the B cells from the patient are isolated from a sample of peripheral blood, bone marrow, or a lymph node biopsy.

8. A method for determining if a human patient suffering from chronic lymphoid leukaemia (CLL) is at risk for disease progression, said method comprising:
   (a) providing a sample comprising B cells from the patient;
   (b) measuring the level of expression of stromal interaction molecule 1 (STIM1) comprising SEQ ID NO: 1 at the plasma membrane surface of the B cells of the sample;
   (c) comparing the measured level of expression of STIM1 to the level of expression of STIM1 expressed on the surface of B cells of a healthy human subject; and
   (d) determining that the patient is at risk for disease progression if the measured level of expression of STIM1 is greater than the level of expression of STIM1 expressed on the surface of B cells of a healthy human subject.

9. The method of claim 8, wherein the level of expression of STIM1 at the plasma membrane surface of the B cells is measured using an immunoassay.

10. The method of claim 9, wherein the immunoassay comprises the use of flow cytometry, microscopy, or an ELISA.

11. The method of claim 8, wherein the B cells from the patient are contacted with an antibody that specifically binds to STIM1.

12. The method of claim 11, wherein that antibody that specifically binds to STIM1 binds to a polypeptide comprising SEQ ID NO: 3.

13. The method of claim 9, wherein the B cells from the patient are contacted with an antibody that specifically binds to CD19 or CD20.

14. The method of claim 8, wherein the B cells from the patient are isolated from a sample of peripheral blood, bone marrow, or a lymph node biopsy.

15. The method of claim 8, wherein the patient is undergoing treatment for CLL.

16. The method of claim 15, wherein said treatment comprises administering to the patient an antibody that specifically binds to CD20.

17. The method of claim 16, wherein said antibody that specifically binds to CD20 is Rituximab, DB00073, Ofatumumab, Tositumomab, Obinutuzumab, Ibritumomab, Ublituximab, or AME-133v.

* * * * *